United States Patent [19]
Thompson

[11] Patent Number: 6,055,990
[45] Date of Patent: May 2, 2000

[54] POLYMERIZING GEL INTRAKERATOPHAKIA-PGI

[76] Inventor: Keith P. Thompson, 4338 Town Commons Cir., NE., Atlanta, Ga. 30319

[21] Appl. No.: 09/063,521

[22] Filed: Apr. 21, 1998

Related U.S. Application Data

[60] Provisional application No. 60/043,739, Apr. 21, 1997.

[51] Int. Cl.[7] ..................... A61B 19/00
[52] U.S. Cl. ............ 128/898; 623/4.1; 623/5.11; 606/5
[58] Field of Search ............ 623/4, 6, 4.1, 5.11; 606/1, 4, 5, 6, 107, 201; 128/897, 898; 424/422, 424, 427

[56] References Cited

U.S. PATENT DOCUMENTS

| | | | |
|---|---|---|---|
| 4,923,467 | 5/1990 | Thompson | 623/5 |
| 4,969,912 | 11/1990 | Kelman et al. | 623/66 |
| 5,104,408 | 4/1992 | Thompson | 623/5 |
| 5,156,622 | 10/1992 | Thompson | 623/5 |
| 5,163,956 | 11/1992 | Liu et al. | 623/4 |
| 5,522,888 | 6/1996 | Civerchia | 623/4 |
| 5,716,633 | 2/1998 | Civerchia | 424/428 |

*Primary Examiner*—Michael J. Milano
*Assistant Examiner*—Dinh X. Nguyen
*Attorney, Agent, or Firm*—James W. Kayden; Thomas, Kayden, Horstemeyer & Risley

[57] ABSTRACT

A method, materials, and medical devices are disclosed for providing an intralamellar insert between opposing layers formed in the cornea. Upon preparing the cornea by partially separating a flap of tissue, a gel or similar material is placed thereon and conformed to desired dimensions to correct refractive errors of the cornea.

11 Claims, 2 Drawing Sheets

POLYMERIZING GEL INTRAKERATOPHAKIA-PGI

This application claims priority to U.S. Provisional Patent Application Serial No. 60/043,739, filed Apr. 21, 1997.

BACKGROUND OF THE INVENTION

Numerous methods, ophthalmic devices, and medical equipment are available to surgeons to alter the refractive power of the eye. One of the most common methods involves altering the anterior corneal curvature, which comprises approximately ⅔ of the eye's optical power. Such surgical methods presently in use include radial keratotomy (RK), excimer laser photorefractive keratectomy (PRK) laser and in-situ Keratomileusis (LASIK). None of these techniques correct a full range of refractive errors, nor have they been found to correct irregular astigmatism, a problem encountered in many patients following previous refractive surgical procedures, corneal trauma, keratoconus, and other conditions that produce an abnormal corneal shape. LASIK and PRK require irreversible removal of corneal tissue.

SUMMARY OF THE INVENTION

A method and the accompanying medical devices and equipment for altering the refractive corneal power of the human or other mammalian eye is described whereby a gel material is placed under a lamellar flap of corneal tissue. The dimensions of the gel in the bed formed in the cornea alter the anterior corneal curvature to correct refractive errors of the cornea. Molding the cornea with the gel in place with the use of a mold held to the anterior surface can change corneal power in a predictable fashion, treating myopia, hyperopia, and regular or irregular astigmatism.

While the following description teaches a method and the preferred material and devices for accomplishing correction of refractive errors, various additional changes and modifications may be made without departing from the scope of the present invention.

DETAILED DESCRIPTION OF THE PREFERRED EMBODIMENT

This invention describes a method, the devices, and the materials used for altering corneal shape which does not involve removing corneal tissue, which is reversible, and which may be adjusted at a later date. Although the present invention may be most useful for procedures where net tissue addition is desirable, such as treatment of hyperopia, it is also likely that it will be effective for treating myopia, astigmatism, and irregular astigmatism. This is shown in FIGS. 1–5 and described hereinbelow.

First, a lamellar flap 10 of corneal tissue in the anterior corneal cap 12 is made. This flap thickness is usually to a depth of approximately 130 to 160 microns, and comprises a corneal diameter of approximately 8.0 to 9.5 mm. Such a corneal flap is made easily with presently available microkeratomes (not shown), such as the Corneal Shaper microkeratome manufactured by Chiron Corporation (Irvine, Calif.).

Figure 1:
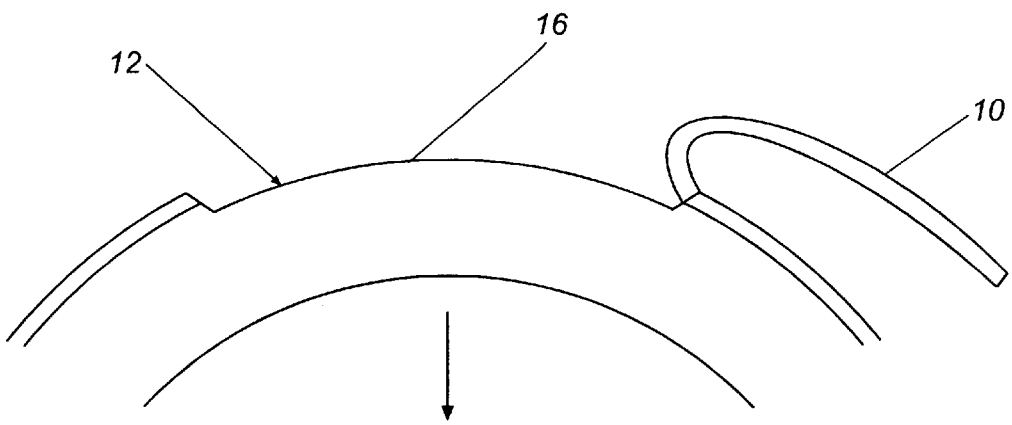
FIG. 1 is a partial diagrammatic side elevational view, illustrating the preparation of the cornea.
Figure 2:
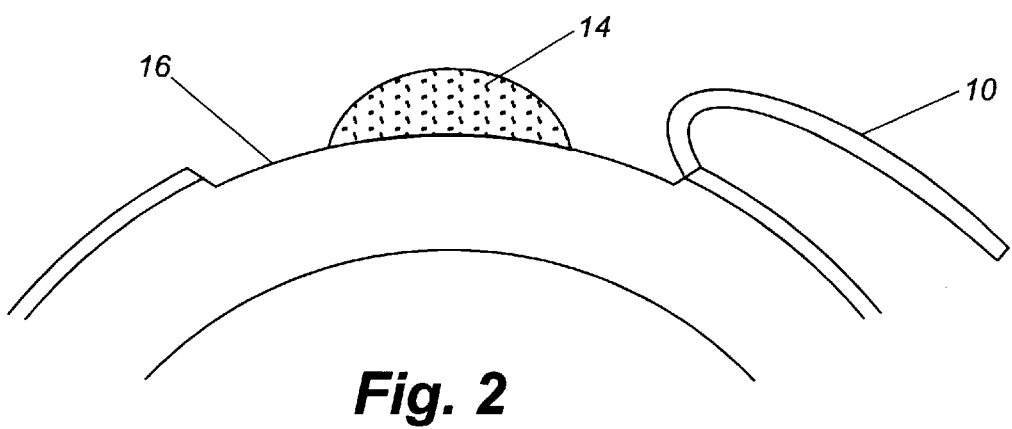
FIG. 2 is a partial diagrammatic side elevational view, illustrating the initial placement of a gel material on the prepared cornea.

Following creation of the corneal flap, the flap is temporarily reflected to the side exactly as it is in the LASIK procedure. A discrete quantity of gel material 14 is placed on the bed 16 of the flap, as shown in FIG. 2. The volume of the gel material may be predetermined by the intended refractive change. In a preferred embodiment of the invention, the gel material will polymerize, that is "set up", after a predetermined period of time. Thus, the gel material 14, as one of its characteristics, will have the property of polymerizing or becoming more solid with a short passage of time after it is placed in the corneal bed 16. Other appropriate materials, such as a solid lenticule, may also be employed.

Figure 3:
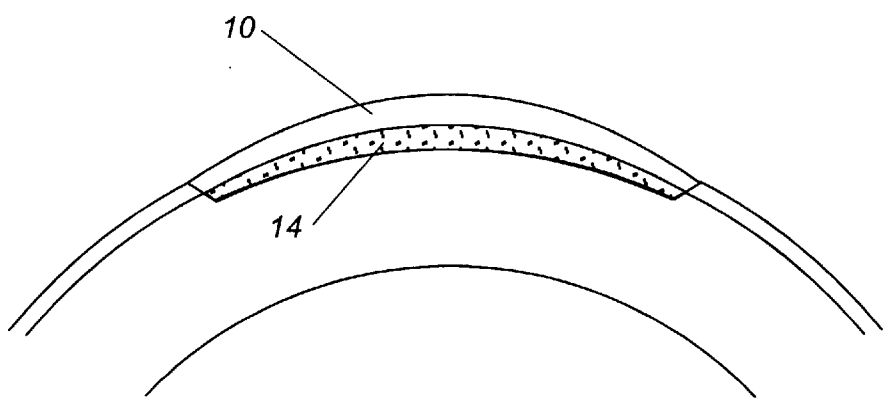
FIG. 3 is a diagrammatic side elevational view showing the gel positioned beneath the corneal flap.
Figure 4:
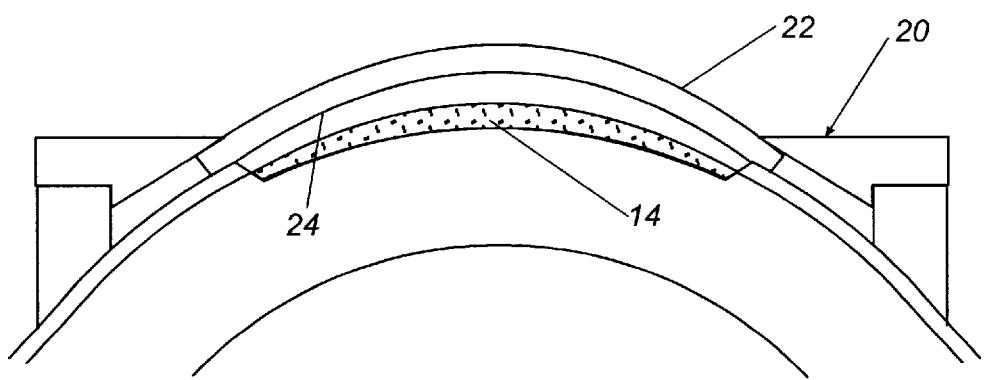
FIG. 4 is a diagrammatic side elevational view showing a molding device applied to the cornea.
Figure 5:
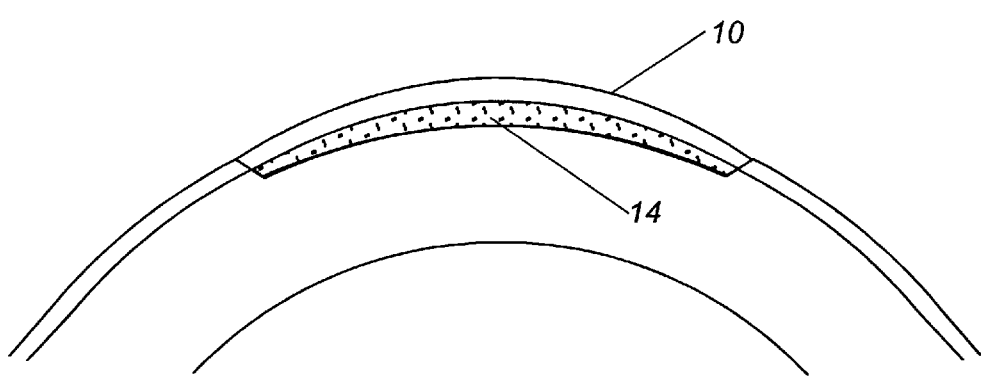
FIG. 5 is a diagrammatic side elevational view showing the resulting intralamellar application.

After placing the gel material, the surgeon replaces the flap into position over the gel, as shown in FIG. 3. Using a suction device which may be operatively associated with the commonly employed microkeratome, a suction mold 20 is affixed to the corneal surface for a predetermined period of time, as illustrated in FIG. 4. When suction is activated, the suction ring 22 drives the cornea into the mold which has a shape and curvature matching the desired dimension of the cornea following treatment. The viscous nature of the gel allows the anterior corneal cap to assume the shape of the posterior surface 24 of the mold 20. As alternatives for conforming the corneal cap and gel, pressure may be applied thereto without utilizing suction, the gel may be configured to the appropriate dimensions prior to placement, the gel can be expandable, or other appropriate means may be employed to achieve the desired result.

Because the gel allows the corneal flap to be lifted into a new position, the anterior corneal cap 12 is free to "float" into a new shape and curvature that matches the posterior curvature of the mold. The suction pressure is released and the gel polymerizes into position. Once the gel is polymerized, the anterior flap is held into its new position. Epithelial cells at the margin of the flap quickly heal, exactly as they do following the standard LASIK procedure.

Postoperative care of the patient is exactly the same as performed with the present LASIK procedure. Little postoperative attention is needed, and routine antibiotic drops for 3–4 days are prescribed. Because the gel polymerizes and holds the flap into its new position, and the cornea has not been structurally destabilized as it has following RK and other procedures, the structural integrity of the cornea is maintained. Wound healing is not invoked and there are no significant epithelial stromal interactions. The outcome of surgery is expected to be stable and will not be influenced by the effects of epithelialstromal wound healing as it is, for example, following excimer laser photorefractive keratectomy and radial keratotomy.

Because no corneal tissue is removed, it is possible to surgically open the flap and peel out the gel, making polymerizing gel intrakeratophakia (PGI) a reversible technique. By using a number of different mold profiles available for attachment and use with the suction ring, and by varying the diameter of the flap, the surgeon can treat a wide variety of refractive errors when the desired radius of curvature of the anterior corneal cap is determined.

I claim:

1. A method of adjusting the refractive power of the cornea comprising the steps of:
   determining the desired radius of curvature of the anterior corneal cap;
   separating a flap of the corneal tissue from said anterior corneal cap, thereby forming a bed in said cap;
   placing a gel material on said cap and repositioning said flap over said gel material;
   attaching a molding device over said flap, said molding device having a defined posterior mold profile;
   applying pressure to conform said cap and gel to said profile; and
   removing said molding device thereby allowing said cap and gel to retain said profile.

2. The method of claim 1, wherein the adjustment of the refractive power of the cornea is reversible, the structural integrity of the cornea is maintained, and no significant epithelial stromal interactions occur.

3. The molding device of claim 1, wherein different mold profiles are available for attachment and use with the molding device.

4. The method of claim 1, wherein the flap may be varied in diameter.

5. A method for adjusting the refractive power of the cornea by changing the radius of curvature of the anterior corneal cap, comprising the steps of:
   determining the desired radius of curvature of said anterior corneal cap;
   separating a flap of the corneal tissue from said anterior corneal cap, thereby forming a bed in said cap;
   placing a predetermined volume of gel material on said cap and repositioning said flap over said gel material;
   attaching a molding device over said flap, said molding device having a defined posterior mold profile;
   applying pressure to conform said cap and gel to said profile; and
   removing said molding device thereby allowing said cap and said gel to retain said profile.

6. The method of claim 5, wherein the adjustment of the refractive power of the cornea is reversible, the structural integrity of the cornea is maintained, and no significant epithelial stromal interactions occur.

7. The molding device of claim 5, wherein different mold profiles are available for attachment and use with the molding device.

8. The method of claim 5, wherein the flap may be varied in diameter.

9. A method of adjusting the refractive power of the cornea by changing the radius of curvature of the anterior corneal cap, comprising the steps of:
   determining the desired radius of curvature of said anterior corneal cap;
   separating a flap of corneal tissue from said anterior corneal cap, thereby forming a bed in said cap;
   placing a solid lenticule on said cap and repositioning said flap over said lenticule.

10. The method of claim 9, wherein the adjustment of the refractive power of the cornea is reversible, the structural integrity of the cornea is maintained, and no significant epithelial stromal interactions occur.

11. The method of claim 9, wherein the flap may be varied in diameter.

* * * * *